United States Patent [19]

Falcone et al.

[11] Patent Number: 5,166,070
[45] Date of Patent: Nov. 24, 1992

[54] VECTORS FOR THE CLONING AND EXPRESSION OF HETEROLOGOUS GENES IN YEAST AND THE YEAST STRAINS TRANSFORMED BY SAID VECTORS

[75] Inventors: Claudio Falcone, Rome, Italy; Hiroshi Fukuhara, Gif sur Yvette, France; Laura Frontali; Michele M. Bianchi, both of Rome, Italy

[73] Assignees: Consiglio Nazionale delle Ricerche; Univ. Degli Studi di Roma, both of Italy

[21] Appl. No.: 431,719

[22] Filed: Nov. 3, 1989

Related U.S. Application Data

[63] Continuation-in-part of Ser. No. 363,384, Jun. 5, 1989, abandoned, which is a continuation of Ser. No. 31,061, Mar. 27, 1987, abandoned.

[30] Foreign Application Priority Data

Mar. 27, 1986 [IT] Italy ............................... 47830 A/86

[51] Int. Cl.$^5$ .................. C12N 15/04; C12N 15/81
[52] U.S. Cl. .................. 435/255; 435/320.1; 435/172.3; 435/69.9; 435/911; 536/27
[58] Field of Search .................. 435/69.1, 172.3, 255, 435/256, 320, 320.1; 536/27

[56] References Cited

FOREIGN PATENT DOCUMENTS 8304261 12/1983 PCT Int'l Appl. .

OTHER PUBLICATIONS

Chen et al, J. Basic Microbiol. 28:4 211-220 (1988) A Gene Cloning System for *Kluyveromyces lactis*.
Das et al, Current Genetics 6:123-128 (1982) A High Frequency Transformation System for . . . Kluyveromyces.
Sreekrishna et al, Gene 28:73-81 (1984) Transformation of *Kluyveromyces lactis* with the Kanamycin . . . gene . . . Tn903.
Chen et al, Current Genetics 16:95-98 (1989) The Host Range of the pKD1-derived Plasmids in Yeast.
Das, S et al; Transformation of *Kluyveromyces fragilis*; J. Bacteriol 158(3) p. 1165 (1984).
Falcone, C et al; Analysis of a 1.6 μm circular plasmid from the yeast *Kluveromyces drosophilarum*: Structure and Molecular Dimorphism; Plasmid 15 p. 248 (1986).
Yamakawa, M et al; Construction of a plasmid—replicating in both *S. cerevisiae* and *Kluyveromyces lactis*; Agric Biol Chem 49(5) p. 1537 (1985).
Laudenbach, D. E. et al; Evidence for two distinct origins of replication in the large endogenous plasmid of *Anacystis nidulans* R2. Mol Gen Genet 199 p. 300 (1985).
Metz, B. A. et al; Identification of an endogenous plasmid in *D. discoideum*; EMBO 2(4) p. 515 (1983).
Santamaria R et al; Characterization of an endogenous plasmid and development of cloning vectors and a transforming system in *Brevibacterium lactofermentum*; J. Gen. Microbiol. 130, p. 2237 (1984).
Gerbaud, C. et al; High frequency of yeast transformation by plasmids carrying part or entire 2-μm yeast plasmid; Gene 5 p. 233 (1979).
EPA 0 095 986, claims and p. 4, line 29–p. 10, line 5.
EPA 0 096 910, p. 8, line 1–p. 10, line 20; p. 19, line 21–p. 20, line 12; claims.
EPA 0 096 430–claims.

(List continued on next page.)

Primary Examiner—Richard A. Schwartz
Assistant Examiner—T. Michael Nisbet
Attorney, Agent, or Firm—Pollock, Vande Sande & Priddy

[57] ABSTRACT

Vectors for the cloning of heterologous genes in yeast, which have the characteristic that they contain at least the entire DNA of the pKD1 plasmid (isolated from *Kluyveromyces drosophilarum*) or a part of the same, as well as a DNA segment bearing any heterologous gene and the sequence necessary for the expression of said gene. The high stability of yeasts transformed by said vectors allows their utilization on an industrial scale in various biotechnological fields.

17 Claims, 4 Drawing Sheets

OTHER PUBLICATIONS

Journal of Bacteriology, vol. 145, No. 1, Jan. 1981, pp. 382–390 Gunge et al "Isolation and Characterization of Linear Deoxyribonucleic Acid Plasmids From *Kluyveromyces lactis* and the Plasmid-Associated Killer Character"; p. 382, col. 2.

Nucleic Acids Research, vol. 14, No. 11, 1986, pp. 4471–4481, Chen et al "Sequence Organization of the Circular Plasmid pKD1 from the Yeast *Kluyveromyces drosophilarum*" (whole article).

Nucleic Acids Research, vol. 12, No. 19, Oct. 1984, pp. 7581–7597 Hishinuma et al "Cloning and Nucleotide of the Linear DNA Killer Plasmis From Yeast".

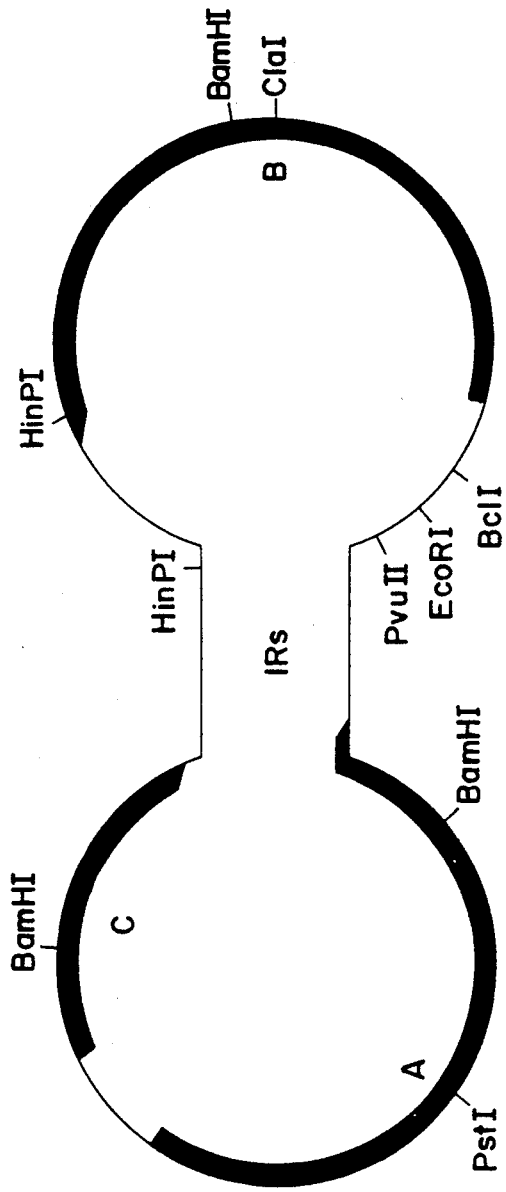
FIG.2 pKD1 (4757bp)

VECTORS FOR THE CLONING AND EXPRESSION OF HETEROLOGOUS GENES IN YEAST AND THE YEAST STRAINS TRANSFORMED BY SAID VECTORS

This application is a continuation-in-part application of Ser. No. 363,384, filed Jun. 5, 1989, now abandoned, which is a continuation of Ser. No. 031,061 to Falcone et al, filed on Mar. 27,1987, both now abandoned

BACKGROUND OF THE INVENTION

The present invention concerns cloning vectors for heterologous genes in yeasts as well as the yeast strains transformed by said vectors.

In more detail, the present invention concerns vectors for the transformation of yeasts, in which vectors the entire nucleotide sequence of the pKD1 plasmid of *Kluyveromyces drosophilarum* or a part of the same is present. Moreover, the present invention concerns specifically yeasts providing functions for a replication of these vectors.

As is well known, the transformation of yeasts up to the present time has been limited to certain species because of the poor availability of the yeast plasmids that are required for the construction of transformation vectors (Gunge, N., Ann. Rev. Microbiol. 37, 253-276 (1983); Toh-e, A., Tada, S. and Oshima, Y., J. Bacteriol. 151, 1380-1390 (1982): Toh-e, A., Arakl, H., Utatsu, I., and Oshima, Y., J. Gen. Microbiol. 130, 2527-2534 (1984).

The $2\mu$ plasmid isolated from Saccharomyces cerevisiae has been, up to the present time, the only plasmid successfully employed for the transformation of said S. cerevisiae. However, vectors derived from the $2\mu$ plasmid have shown a low transformation efficiency and/or a limited ability to replicate stably in yeasts other than *Saccharomyces cerevisiae*.

Accordingly, it was quite evident that plasmids for the construction of vectors suitable for the transformation of other yeasts were needed, especially for yeasts of industrial importance, including, for example, those belonging to the genus Kluyveromyces.

However, all attempts to date to satisfy this need have not been very effective.

More specifically, two vectors have been used for the transformation of *Kluyveromyces lactis:* one contained a chromosomal DNA segment of *K. lactis* (Das, S. and Hollenberg, C. P., Current Genetics 6 123-128 (1982), and the other was derived from the linear plasmid pGK1 also isolated from K. lactis (L. de Louvencourt, H. Fukuhara, H. Heslot, M. Wesolowski, French Patent Application No. 8209564 of ELF Biorecherche; L. de Louvencourt et al., J. Bacteriol. 154, 737742 (1982).

It is important to point out that, although both of the vectors mentioned above contain nucleotide sequences of *K. lactis* that allow their replication in this yeast, the efficiency and/or the stability with which transformed clones are obtained is quite low.

Accordingly, an object of the present invention is the production of cloning vectors for yeasts, in particular for the genus Kluyveromyces, which have improved transformation efficiency and which show a higher stability in the transformed cells.

Now it has been surprisingly found, according to the present invention, that this object can be attained by using as an essential part of the transformation vectors, a plasmid or at least a genetic element thereof discovered in a strain of the yeast *Kluyveromyces drosophilarum*, in the course of a research project on new plasmids (C. Falcone, et al Plasmid, 15 248-252(1986)).

The plasmid dealt with herein consists of a circular duplex DNA molecule of 1.6 micron circumference, which was found in the UCD 51-130 *Kluyveromyces drosophilarum* strain (U.C.D. Collection, University of California, Davis, Calif. 95616). The same strain is available from the American Type Culture Collection (U.S.A.) under the accession No. ATCC 56496, from the Agricultural Research Service Culture Collection (U.S.A.) under the No. NRRL Y-8278 and from the Centraalbureau voor Schimmelcultures (The Netherlands) under the No. CBS 2105.

This plasmid, which is called pKD1, is present in the cells in a high copy number (70-100 per cell) and it is easily separable from the chromosomal DNA by employing standard procedures.

The complete nucleotide sequence of pKD1 has been determined, and so the exact size of the plasmid (4757 base pairs) is known. In addition, the analysis of the sequence confirmed the data previously obtained through DNA-DNA hybridization concerning the substantial difference in primary structure between this plasmid and the $2\mu$ and pGK1 plasmid.

The plasmid exists inside the same cell in two interchangeable molecular forms called A and B, which are present in equal amounts and differ from one another by the orientation of a central segment of 2.15 kilobases that, in FIG. 1 enclosed herein, is comprised between two vertical dashed lines. FIG. 1 shows the localization of the sites for numerous restriction enzymes (such location referring to the A and B forms of pKD1 when drawn as linear molecules), such enzymes being indicated in the left margin of FIG. 1. The scale shown in the horizontal direction points out the distance in kilobases (kb) between these sites on the plasmid. Numbers shown inside the segments indicate their respective lengths in base pairs. The asterisks point out those fragments whose localization was uncertain before the entire sequence was determined.

The analysis of the sequence showed the presence in this plasmid of a DNA segment of 346 base pairs which was found again, identical in sequence but with inverted orientation, at a distance of 2136 nucleotides.

This inverted and repeated (IR) sequence is likely to be fundamental in the mechanism of interconversion between the A and B forms of pKD1, in analogy with what has been observed with the $2\mu$ plasmid of S. cerevisaiae.

From the nucleotide sequence of the plasmid pKD1 the presence of three possible genes, called A, B and C, was deduced (with respective lengths of 1341, 1245 and 636 nucleotides); these genes, based on sequence homologies and preliminary studies on their functions, seem to be analogous, respectively, to the FLP, Rep 1 and Rep $2\mu$ genes that are present in the 2 plasmid (Broach, J. R., Cell 28, 203-204 (1982)).

The pKD1 plasmid can be advantageously employed for the construction of cloning vectors in yeasts, primarily because its circular form allows simple manipulations. Moreover, this plasmid contains numerous unique sites for restriction enzymes, such as EcoRI, ClaI and PstI, and this feature is also particularly advantageous for the insertion of heterologous genes and for the construction of recombinant vectors.

The presence of the pKD1 plasmid and of the vectors derived from the same in the yeast cells at a high copy number is a further advantage because it allows an amplification of the inserted heterologous gene.

Moreover, it is advantageous that neither the integrity nor the continuity of the sequence of the pKD1 plasmid is needed for the construction of stable vectors at a high copy number according to the present invention. Indeed, it is possible to insert the gene to be cloned specifically into one of the unique restriction sites, so interrupting the pKD1 sequence, or to use just a part of this plasmid, containing the replication origin and a segment containing a cis-acting stabilizing sequence (or locus), called CSL.

The specific object of the present invention consists in the construction of cloning vectors for heterologous genes in yeasts, such vectors comprising the entire DNA of the pKD1 plasmid (isolated from *Kluyveromyces drosophilarum*) or a part thereof including at least one genetic element and a DNA segment bearing a heterologous gene and including the sequences that insure the expression of said gene such sequence being derived also from pKD1.

When the entire DNA of the pKD1 plasmid is employed, it is preferable that the gene to be cloned be inserted into one of the unique restriction sites, in particular into the EcoRI or the PstI site.

Among the genes that are most suitable for cloning, the URA3 gene of *S. cerevisiae* is in particular worth considering, preferably as a part of the YIp5 plasmid, which consists of the sequence of the pBR322 plasmid of *Escherichia coli* and, in addition, of the sequence of this URA3 gene.

In another preferred form of the present invention (vector A15), the vector contains the 1717 bp segment of DNA of the B form of the pKD1 plasmid obtained with the enzyme BamHI, inserted into the unique BamHI site of the YIp5 plasmid.

In another preferred embodiment of the present invention (vector HP1), the vector contains the 375 bp DNA segment of the pKD1 plasmid obtained by digestion with the HinPI enzyme, inserted into the unique ClaI site of the YIp5 plasmid.

In a further preferred embodiment (vector HCS1), the cloning vector contains the 207 bp segment of the pKD1 DNA obtained with the restriction enzymes BclI and PvuII, replacing the BamHI-NruI segment of the tetracycline resistance gene of the HP1 vector.

The present invention also relates to yeasts transformed by the above-mentioned vectors and, particularly but not exclusively, to the strains of the genus Kluyveromyces and more specifically of the species *Kluyveromyces lactis*. While the Kluyveromyces genus is of particular interest since it has been found that the pKD1 plasmid can replicate in the Kluyveromyces strains with variable stability, the present invention is intended to cover the transformation of all yeasts in which the pKD1 plasmid is able to replicate, whether or not such yeast is classified at a given time under the Kluyveromyces genus. For example, it has been demonstrated that yeasts which have been classified as Candida are actually Kluyveromyces. Martini A. V. and Martini A., Int. J. Syst. Bacteriol. Vol. 37, p. 380–385, 1986, reported DNA-DNA reassociation experiments which demonstrated that C. macedoniensis and K. Marxianus have high DNA sequence homology and Sor F. and Fukuhara H., Yeast, Vol. 5, p. 1-10, 1989, confirmed that hypothesis by analysis of chromosomal migration patterns and mitochrondrial DNA.

It is interesting to note that yeasts transformed according to the present invention can be advantageously exploited for the production of the protein coded by the heterologous gene inserted into the vector. Such yeasts can be, for example, of remarkable importance in the foodstuff field (the production of amylase, rennin, pectinase and so on) or in the pharmaceutical field (insulin, interferon and so on).

In addition, such transformed yeasts can constitute in themselves integrating products for the feeding of animals or livestock (biomass).

For the sake of discussion, and for illustrative but not limitative purposes, the use of the invention for the cloning of the URA3 gene of *Saccharomyces cerevisiae* in a uraA strain of *Kluyveromyces lactis* will be considered. The uraA strain is normally unable to grow in uracil-free medium. The URA3 gene that is present in vectors derived from the pKD1 plasmid was shown to be expressed in the host cell and such cells were shown to be able to grow in uracil-free mediums. This shows that the orotidine-monophosphate decarboxylase protein encoded by the URA3 gene of *S. cerevisiae* is effectively synthesized by K. lactis.

BRIEF DESCRIPTION OF THE FIGURES

FIG. 2 schematically shows the structure of the B form of the pKD1 plasmid;

DETAILED DESCRIPTION OF THE INVENTION THE CONSTRUCTION OF VECTORS DERIVED FROM THE pKD1 PLASMID THAT CONTAIN THE URA3 GENE

The Isolation And Purification Of The pKD1 Plasmid

The plasmid DNA was prepared from the protoplasts obtained from 2 1 of a culture of *K. drosophilarum*. Nucleic acids obtained after lysis of the protoplasts were resuspended in 40 ml of a solution containing 50 mM Tris-HCl, 5 mM EDTA, pH 8.0. 40 g of CsCl and 4 ml of ethidium bromide (10 mg/ml in 50 mM Tris-HCl, pH 8.5) were added to the DNA-containing solution which was then centrifuged at 38,000 rpm in a Beckman 50 Ti rotor for 40 hours at 15° C. The DNA was visualized with U.V. light and the lower band, corresponding to the plasmid DNA, was recovered from the gradient and purified a second time according to the procedure described above.

pKD1-Derived Vectors

Reference will now be made in a specific way to FIG. 2 in which pKD1 is shown in the circular closed form with the inverted and repeated (IR) sequences paired to one another. The A, B and C genes are indicated by black blocks, straight lines correspond to the IR sequences and some important restriction sites are also indicated, including the two HinPI restriction sites delimiting the DNA segment containing the origin of replication. The cis-acting stabilizing locus (CSL) is contained in the BclI-PvuII segment of pKD1.

In this Figure, the B form of plasmid is shown. The form differs from the A form by the orientation of the circle on which the gene A is localized, as already detailed above.

Figure 3:
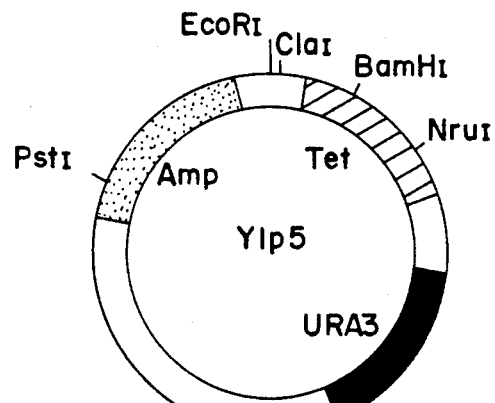
FIG. 3 shows the YIp5 plasmid.

For the construction of recombinant plasmids, pKD1 was first linearized at the unique EcoRI site. At the same time, YIp5, which is a recombinant plasmid containing sequences of the URA3 gene of *Saccharomyces cerevisiae* and of the bacterial plasmid pBR322 was also linearized at the EcoRI site. The structure of YIp5 is shown in FIG. 3, in which the sequences of the URA3 gene of S. cerevisiae are shown in black, and dots and hatches indicate the genes of pBR 322 that are responsible for the resistance to ampicillin (Amp) and tetracycline (Tet), respectively. Furthermore, the position of some unique restriction sites used for cloning are shown.

The two linearized molecules were joined at the common EcoRI site by DNA ligase according to a well-known standard procedure.

The plasmid obtained by this ligation thus contains the entire pKD1 sequence, the URA3 gene and the pBR322 sequence. The latter sequence was introduced with the aim of amplifying the constructed vectors in the bacterium *Escherichia coli*.

The ligation reaction mixture was added directly to a suspension of *E. coli* cells of the strain RR1, which had been made competent for transformation after treatment with calcium chloride.

The cell suspension was plated on a solid ampicillin-containing complete medium. Among the thousands of colonies obtained (which, therefore, were ampicillin-resistant) some tens were transferred on tetracycline-containing media. All were tetracycline-resistant, and were examined individually for the nature of the plasmid they contained.

Figure 1:
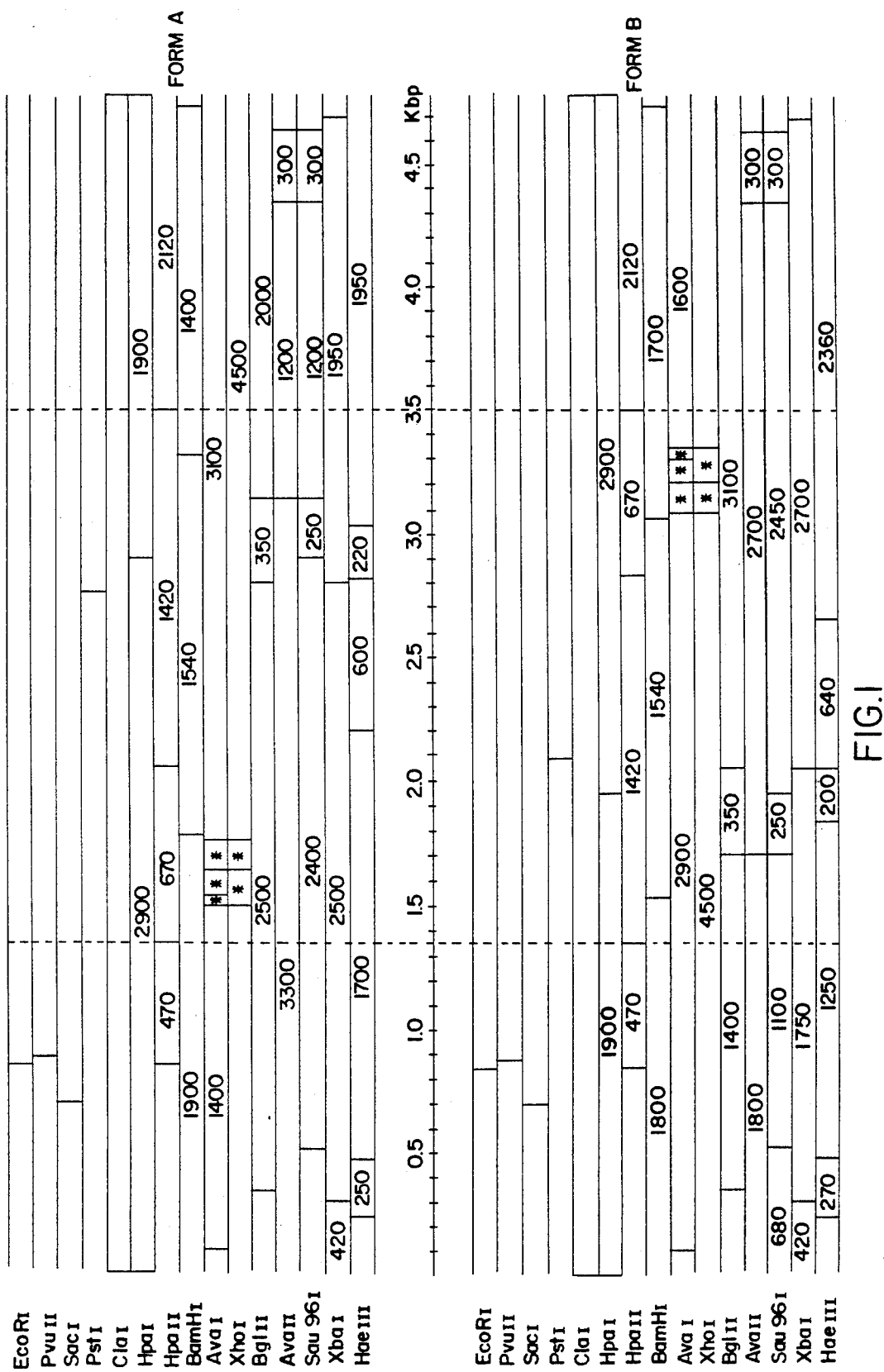
FIG. 1 is a map of the A and B forms of pKD1 plasmid.
Figure 4:
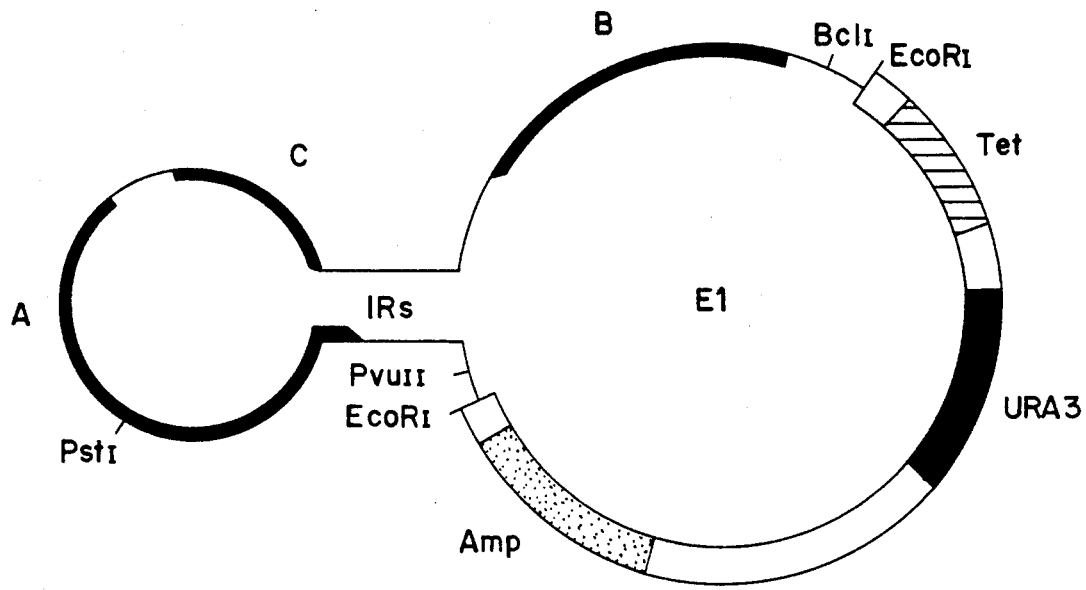
FIG. 4 shows the E1 vector according to the present invention.

It was found that about half of such colonies contained recombinant plasmids having the desired structures. Since pKD1 plasmid exists in two isomeric forms, form A and form B, and insertion to the EcoRI site can occur in both orientations with respect to the YIp5 vector, four different recombinant plasmids were obtained, differing from each other for the isomeric form of pKD1 DNA and for the orientation with respect to the YIp5 vector. The four recombinant vectors were called E1, E3, E4 and E7. The vector E1, shown in FIG. 4, was subsequently used for the experiments of transformation of *Kluyveromyces lactis*.

Another set of vectors containing the complete sequence of pKD1 plasmid and YIp5 plasmid was obtained as follows. The pKD1 DNA was linearized at the unique PstI site, while the YIp5 vector was linearized at the PstI site, which is located within the ampicillin resistance gene. The two molecules were ligated together and transformed into *Escherichia coli* competent cells. Bacterial transformants were selected on tetracycline-containing medium, and tetracycline-resistant-ampicillin-sensitive transformants were examined for the plasmid they contained. Between the recombinant molecules obtained, two vectors were chosen which contained the complete pKD1 DNA sequence in the B form in one case (P1 vector) and in the A form in the other (P3 vector). In the P1 and P3 vectors, the pKD1 DNA sequence had opposite orientation with respect to the YIp5 vector.

The A15 plasmid is another recombinant molecule derived from pKD1. The latter was digested with the restriction enzyme by BamHI and a fragment of 1717 base pairs was isolated. This fragment was then mixed with the linearized molecule of YIp5, which had been cut at its unique BamHI site. After ligation and amplification in *E. coli*, as described above, a clone was selected that shows resistance to ampicillin and sensitivity to tetracycline. A recombinant plasmid was isolated from this clone, and the plasmid contained, as expected, the BamHI fragment of pKD1, the URA3 gene and the sequence of pBR322.

Figure 5:
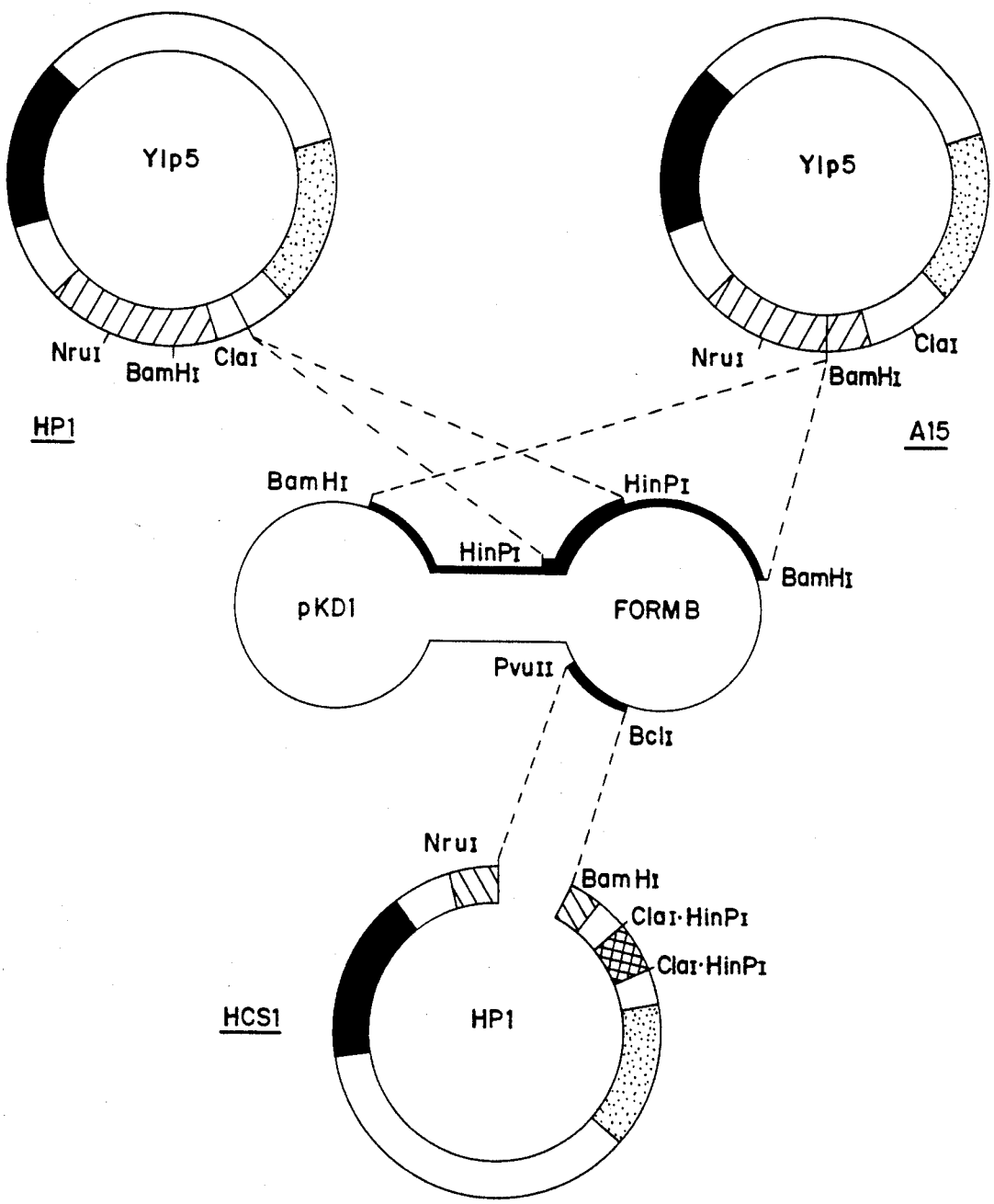
FIG. 5 shows the construction of the vectors A15, HP1 and HCS1 schematically.

In FIG. 5, which relates, inter alia, to the construction of the A15 vector the insertion point of the 1717 bp BamHI fragment (in black) of pKD1 in the YIp5 plasmid is shown. Symbols adopted are the same as those employed in the preceding figures.

Following the same procedure, a 375 base pair segment of pKD1 DNA, obtained by HinPI digestion of the latter plasmid, was introduced at the unique ClaI restriction site of YIp5. The recombinant plasmid containing said segment was called HP1 and it is shown in FIG. 5. *Escherichia coli* cells transformed with HP1 vector were ampicillin-resistant-tetracycline-sensitive and the presence of the 375 bp segment in YIp5 was confirmed by restriction analysis on HP1 DNA preparations. Subsequently, the HP1 vector was digested with the restriction enzymes BamHI and NruI, and the 597 bp BamHI-NruI segment from the tetracycline resistance gene was replaced by the 207 bp BclI-PvuII, of pKD1 DNA. Bacterial transformants were selected for ampicillin resistance and the desired recombinant molecules were detected by restriction analysis. The BclI-PvuII segment of pKD1 DNA was called CS1 and contained the CSL element of pKD1 plasmid. The recombinant HP1 vector containing the CS1 segment was called HCS1. Vectors HP1 and HCS1 are shown in FIG. 5.

The vectors constructed as discussed above using pKD1, the URA3 gene and the sequences of pBR322 that allow replication in *E. coli*, were purified from the clones of *E. coli* previously described and then used for the transformation of a uraA strain of Kluyveromyces lactis.

Transformation of *Kluyveromyces lactis*

Previous studies had shown that the uraA mutation of K. lactis could be complemented by the URA3 gene of *S. cerevisiae* (L. de Louvencourt et al., J. Bacteriol. 154, 737–742 (1982)). Therefore, strains of *K. lactis* containing this mutation were used to verify the transformation with hybrid plasmids consisting of pKD1 sequences and the URA3 gene.

The strain MW98-8C (alpha, uraA, arg, lys), isolated in the Orsay Laboratories from the CBS2359 strain of *Kluyveromyces lactis*, was cotransformed with pKD1 DNA and the recombinant P1 vector. Some ura+ transformant clones were analyzed for the presence of pKD1 plasmid. The clones containing the latter plasmid at high copy number, i.e., optically visible after gel electrophoresis and ethidium bromide staining of DNA minipreparations of the clones, were cured of the recombinant P1 vector. One cured clone was isolated, which contained stably the pKD1 plasmid at high copy number, pKD1+ strain. *K. lactis* strains were grown in liquid medium containing 2% glucose, 1% yeast extract and 1% bactopeptone, for 18 hours at 28° C. in a shaker bath.

The cells, in the phase of exponential growth, were converted into protoplasts according to a standard procedure.

The protoplasts were resuspended in STC buffer (1M sorbitol, 10 mM CaCl$_2$, 10 mM Tris-HCl, pH 7.5) at a concentration of about $10^9$ per ml. An aliquot of this suspension, usually 0.1 ml, was then mixed with 0.2–0.5 g of the E1, E7, HP1, HCS1, P1, P3 and A15 vectors described in the present invention and of the control plasmids.

After 10 minutes, the suspension was mixed with one volume of polyethylene glycol 4000. After a further period of 10 minutes at room temperature, the suspension was centrifuged, and the spheroplasts were resuspended in SOS buffer (100 ml of the latter contain: 50 ml of 2M sorbitol, 33.5 ml of YEP medium, 0.65 ml of 1M $CaCl_2$, 135 $\mu$l of 1% uracil and 15 ml of water, and held at 30° C. for one hour).

Aliquots of the spheroplast suspension were added to 4 ml of W medium (minimum medium), which was kept liquid at 45° C. and contained the supplements that complemented the auxotrophies other than uracil. The resulting suspension was then poured onto Petri dishes containing solid W medium.

The growth of colonies was observed after 3–4 days incubation at 28° C.

The efficiency of transformation was $1-5 \times 10^4$ ura+ transformants per 0.2 $\mu$g DNA per $10^8$ protoplasts.

Table 1 below shows examples of the stabilities of transformants, obtained with the vectors derived from the pKD1 plasmid. pKD1° and pKD1+ indicate the absence or the presence of such plasmid in the transformed cells.

TABLE 1

| Vector | Stability (a) pKD1° | (pKD1+) |
|---|---|---|
| E1 | 87 | 66 |
| E7 | 50 | 51 |
| p1 | 46 | 42 |
| P3 | 38 | 48 |
| A15 | 6.3 | 40 |
| HP1 | 4.5 | 11 |
| HCS1 | 1.8 | 67 |

(a) Stability is expressed as the percentage of ura⁻ colonies obtained after six generations in nonselective medium.

Only those protoplasts to which a pKD1 sequence-containing plasmid was added gave rise to the formation of colonies that are therefore ura+. In the case of YIp5, which does not contain any pKD1 sequences, colonies were observed only after addition of uracil to the growth medium.

DNA was extracted from some colonies transformed with pKD1-derived vectors, and the presence of a plasmid whose restriction map was identical to the map of the plasmid used for the transformation was observed.

As can be observed in the Table, the smallest pKD1 DNA fragment sufficient to promote the replication of the recombinant vectors in *Kluyveromyces lactis* is the 375 bp HinPI fragment contained in the HP1 vector. However, the stability of this vector is rather low in both pKD1° and pKD1+ transformants. Very high stability can be obtained if the 207 bp BclI-PvuII fragment is also contained in the recombinant vector (HCS1), but only when pKD1+ strains were transformed.

These results indicate that the BclI-PvuII segment of pKD1 DNA, called CS1, contains some cis-acting element of pKD1 plasmid that could have an important role in the plasmid maintenance, but some trans-acting factors encoded by the pKD1 plasmid are required for high stability of the recombinant vector. The highly stable HCS1 vector contains only 582 (375+207) bp of the pKD1 DNA. On the other hand, the stability of the pKD1+ and pKD1° transformants obtained with the E1 vector, which contains the entire pKD1 plasmid, is by far the highest observed to date in the transformation of Kluyveromyces.

This is highly advantageous for industrial applications involving yeasts transformed by these vectors.

The present invention has been discussed with particular reference to some specific aspects, but it is to be understood that modifications and, changes can be introduced by those who are skilled in this field without departing from the spirit and scope of the invention. For example, this invention may be used to transform any yeast in which the pKD1 plasmid is able to replicate and the invention is not limited to those yeasts which are classified under the Kluyveromyces genus. Workers in the art can, by following the teachings herein, determine by routine experimentation whether a specific strain of yeast can be transformed in accordance with this invention which is to be limited only according to the claims appended hereto and equivalents thereof.

What is claimed is:

1. A cloning vector for the expression of heterologous genes in a yeast, which vector is capable of replication in said yeast which vector comprises at least one pKD1 derived sequence selected from the group consisting of an autonomous replication sequence, a CIS-acting stabilizing sequence, and inverted repeated sequences, and a DNA segment bearing a heterologous gene and including sequences that insure the expression of said gene.

2. A cloning vector according to claim 1 wherein said pKD1 derived sequence is the origin of replication.

3. A cloning vector according to claim 1 wherein said pKD1 derived sequence is the cis-acting stabilizing sequence.

4. A cloning vector according to claim 1 wherein said pKD1 derived sequence is an Inverted Repeated Sequence.

5. A cloning vector according to claim 1 comprising the entire sequence of pKD1 plasmid.

6. A cloning vector according to claim 1 wherein said DNA segment is inserted into one of the unique restriction sites of said pKD1 plasmid.

7. A cloning vector according to claim 6 wherein said unique restriction site is selected from EcoRI or PstI.

8. A cloning vector according to any one of claims 1–7 wherein said DNA segment contains the URA3 gene of Saccharomyces cerevisiae and its native promoter.

9. A cloning vector according to claim 8 wherein said DNA segment containing said URA3 gene and its native promoter is the YIp5 plasmid linearized.

10. A cloning vector according to claim 1 wherein said DNA segment is the YIp5 plasmid linearized with BamHI and said genetic element of the pKD1 plasmid is comprised within the 1717 bp BamHI fragment derived from the B form of pKB1.

11. A cloning vector according to claim 1 wherein said DNA segment is the YIp5 plasmid linearized with ClaI and said genetic element of the pKD1 plasmid is comprised within its 375 bp HinPI fragment.

12. A cloning vector according to claim 1 wherein said DNA segment is the YIp5 plasmid lacking the BamHI-NruI fragment of its tetracycline resistant gene and said genetic element of the pKD1 plasmid is comprised within its 207 bp 13. Cloning vectors for expression of heterologous genes according to any one of claims 1-7, or 10-12, wherein said yeasts able to supply functions for their stable replication belong to the Kluyveromyces genus.

14. Yeast transformed by and able to supply functions for stable replication of the vector claimed in any of claims 1-7, or 10-12.

15. Yeast according to claim 14 of the genus Kluyveromyces.

16. Yeast according to claim 15 of the species *K. lactis*.

17. Yeast according to claim 15 of the species *K. drosophilarum*.

* * * * *